United States Patent
Lim et al.

(10) Patent No.: US 8,602,827 B2
(45) Date of Patent: *Dec. 10, 2013

(54) TERMINAL CONNECTOR ASSEMBLY FOR A MEDICAL ELECTRICAL LEAD

(71) Applicants: Lily Lim, Minneapolis, MN (US); Ronald W. Kunkel, Jim Falls, WI (US); Joseph Walker, Shoreview, MN (US); Peter Hall, Andover, MN (US); Steven E. Schultz, West Lakeland, MN (US); Devon N. Arnholt, Shoreview, MN (US); Angelo Fruci, Mahtomedi, MN (US)

(72) Inventors: Lily Lim, Minneapolis, MN (US); Ronald W. Kunkel, Jim Falls, WI (US); Joseph Walker, Shoreview, MN (US); Peter Hall, Andover, MN (US); Steven E. Schultz, West Lakeland, MN (US); Devon N. Arnholt, Shoreview, MN (US); Angelo Fruci, Mahtomedi, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/739,490

(22) Filed: Jan. 11, 2013

(65) Prior Publication Data
US 2013/0137312 A1 May 30, 2013

Related U.S. Application Data

(63) Continuation of application No. 12/948,499, filed on Nov. 17, 2010, now Pat. No. 8,382,529.

(60) Provisional application No. 61/291,191, filed on Dec. 30, 2009.

(51) Int. Cl.
*H01R 24/04* (2006.01)

(52) U.S. Cl.
USPC ............................................. 439/669; 439/909

(58) Field of Classification Search
USPC .................... 439/668, 669, 909; 607/37, 119
See application file for complete search history.

(56) References Cited

U.S. PATENT DOCUMENTS

| 3,657,744 | A |   | 4/1972  | Ersek |
| 5,056,517 | A |   | 10/1991 | Fenici |
| 5,304,219 | A |   | 4/1994  | Chernoff et al. |
| 5,385,409 | A |   | 1/1995  | Ide |
| 5,487,757 | A |   | 1/1996  | Truckai et al. |
| 5,669,790 | A | * | 9/1997  | Carson et al. ............... 439/668 |
| 6,026,567 | A |   | 2/2000  | Swoyer et al. |
| 6,434,430 | B2|   | 8/2002  | Borgersen et al. |
| 6,623,480 | B1|   | 9/2003  | Kuo et al. |
| 6,650,921 | B2|   | 11/2003 | Spehr et al. |
| 6,725,096 | B2|   | 4/2004  | Chinn et al. |
| 6,785,576 | B2|   | 8/2004  | Verness |
| 6,792,317 | B1|   | 9/2004  | Doan et al. |

(Continued)

OTHER PUBLICATIONS

International Search Report and Written Opinion issued in PCT/US2010/057025 dated Mar. 2, 2011.

*Primary Examiner* — Hien Vu
(74) *Attorney, Agent, or Firm* — Faegre Baker Daniels LLP

(57) ABSTRACT

An IS-4 terminal connector assembly includes three terminal electrodes positioned over an inner tubular member such that they are radially offset from one another. Each of the terminal ring electrodes are configured such that they can withstand both tensile and cyclical bending loads with minimal compromise in their outer geometry. Additionally, each of the terminal electrodes is configured such that they have both an inner and outer geometry that facilitates adequate insulation between a select terminal electrode and an adjacent conductor. Additionally, each of the terminal ring electrodes is configured such that they facilitate an external approach to staking a cable conductor.

14 Claims, 8 Drawing Sheets

(56) References Cited

U.S. PATENT DOCUMENTS

| | | |
|---|---|---|
| 6,912,423 B2 | 6/2005 | Ley et al. |
| 7,160,311 B2 | 1/2007 | Blatter et al. |
| 7,175,478 B2 | 2/2007 | Ollivier |
| 7,234,977 B2 * | 6/2007 | Westlund et al. .............. 439/736 |
| 7,648,401 B2 * | 1/2010 | Guenther et al. .............. 439/669 |
| 7,962,213 B2 | 6/2011 | Arnholt et al. |
| 8,126,557 B2 * | 2/2012 | Jang et al. ....................... 607/37 |
| 8,437,866 B2 | 5/2013 | Gebauer et al. |
| 2001/0037135 A1 | 11/2001 | Pianca et al. |
| 2002/0029074 A1 | 3/2002 | Treaba et al. |
| 2002/0077685 A1 | 6/2002 | Sundquist et al. |
| 2003/0023294 A1 | 1/2003 | Krall et al. |
| 2003/0036779 A1 | 2/2003 | Westlund et al. |
| 2003/0074031 A1 | 4/2003 | Ley et al. |
| 2004/0054390 A1 | 3/2004 | Zarembo et al. |
| 2004/0064174 A1 | 4/2004 | Belden |
| 2004/0068313 A1 | 4/2004 | Jenney et al. |
| 2004/0215282 A1 | 10/2004 | Weijden et al. |
| 2004/0215303 A1 | 10/2004 | Sage |
| 2004/0230268 A1 | 11/2004 | Huff et al. |
| 2005/0027325 A1 | 2/2005 | Lahti et al. |
| 2006/0041299 A1 | 2/2006 | Bauer et al. |
| 2006/0259105 A1 | 11/2006 | Gebauer et al. |
| 2007/0027517 A1 | 2/2007 | Bischoff et al. |
| 2008/0027504 A1 | 1/2008 | Bedenbaugh |
| 2008/0046059 A1 | 2/2008 | Zarembo et al. |
| 2008/0114230 A1 | 5/2008 | Addis |
| 2008/0154328 A1 | 6/2008 | Thompson et al. |
| 2011/0159748 A1 | 6/2011 | Lim et al. |
| 2011/0208282 A1 | 8/2011 | Arnholt et al. |

* cited by examiner

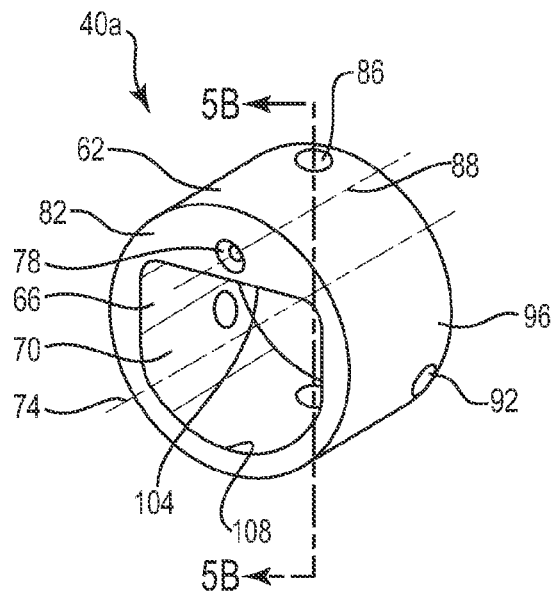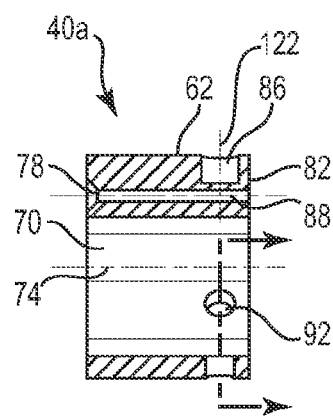
Fig. 5C
Fig. 5A
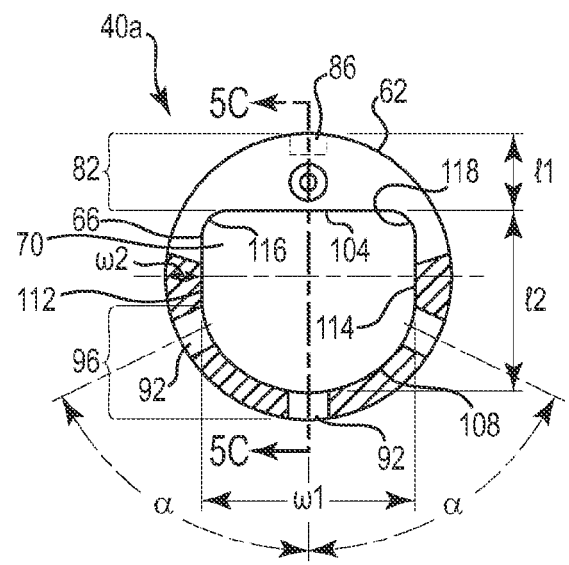
Fig. 5B

TERMINAL CONNECTOR ASSEMBLY FOR A MEDICAL ELECTRICAL LEAD

CROSS REFERENCE TO RELATED APPLICATIONS

This application is a continuation of U.S. application Ser. No. 12/948,499, filed Nov. 17, 2010, which is a non-provisional of U.S. Provisional Application No. 61/291,191, filed on Dec. 30, 2009, which are hereby incorporated herein by reference in their entirety for all purposes.

TECHNICAL FIELD

The present invention relates to medical electrical leads and more particularly, to a terminal connector assembly for a medical electrical lead.

BACKGROUND

Pacemaker leads represent the electrical link between the pulse generator and the heart tissue, which is to be excited and/or sensed. These pacemaker leads include single or multiconductors that are connected to an electrode in an electrode assembly at an intermediate portion or distal end of a pacing lead. A connector is included at the proximal end to form the electrical connection with the pacemaker.

When leads with multiple conductors are involved, the conductors are individually, mechanically and electrically coupled with the pulse generator at a proximal end of the multiple conductors, and can be coupled at a distal end or an intermediate portion with tissue electrodes. The multiple conductors are electrically insulated from each other to prevent shorts and limit electrical leakage between conductors.

SUMMARY

In Example 1, a terminal connector assembly for a medical electrical lead comprises an inner tubular member and a first terminal ring electrode disposed over the inner tubular member. The first terminal ring electrode comprises a first lumen having a generally D-shaped cross-section and defining a first longitudinal axis, an upper portion including a second lumen extending along a second longitudinal axis parallel the first longitudinal axis, and a blind hole having a lower surface formed in an outer surface of the upper portion such that it is disposed over the second lumen. The first terminal ring electrode also comprises a lower portion including at least one aperture extending there through. A first cable is conductor mechanically and electrically coupled within the second lumen of the first terminal ring electrode. The terminal connector assembly further includes a second terminal ring electrode disposed over the inner tubular member such that it is radially offset from the first terminal ring electrode. An insulator is disposed over the inner tubular member and between the first and second terminal ring electrodes such that the first and second terminal ring electrodes are electrically isolated from one another.

In Example 2, the terminal connector assembly according to Example 1, wherein the second terminal ring electrode comprises a first lumen having a generally D-shaped cross-section and defining a first longitudinal axis, an upper portion including a second lumen extending along a second longitudinal axis parallel the first longitudinal axis, and a blind hole formed in an outer surface of the upper portion such that it is disposed over the second lumen. The second terminal ring electrode also includes a lower portion including at least one aperture extending there through.

In Example 3, the terminal connector assembly according to any one of Examples 1-2, wherein the second terminal ring electrode is radially offset from the first terminal ring electrode by about 64°.

In Example 4, the terminal connector assembly according to any one of Examples 1-3, further comprising a second cable conductor mechanically and electrically coupled to the second terminal ring electrode.

In Example 5, the terminal connector assembly according to any one of Examples 1-4, further comprising a third terminal ring electrode disposed over the inner tubular member such that it is radially offset from the second terminal ring electrode and wherein the third terminal ring electrode is electrically isolated by the insulator from the first and second terminal ring electrodes.

In Example 6, the terminal connector assembly according to any one of Examples 1-5, wherein the third terminal ring electrode comprises a first lumen having a generally D-shaped cross-section and defining a first longitudinal axis, an upper portion including a second lumen extending along a second longitudinal axis parallel the first longitudinal axis, and a blind hole formed in an outer surface of the upper portion such that it is disposed over the second lumen. The third terminal ring electrode also includes a lower portion including at least one aperture extending there through.

In Example 7, the terminal connector assembly according to any one of Examples 1-6, further comprising a third cable conductor mechanically and electrically coupled to third terminal ring electrode.

In Example 8, the terminal connector assembly according to any one of Examples 1-7, wherein the third terminal ring electrode is radially offset from the second terminal ring electrode by about 64°.

In Example 9, the terminal connector assembly according to any one of Examples 1-8, further comprising a terminal pin coupled to a coiled conductor extending within the inner tubular member.

In Example 10, the terminal connector assembly according to any one of Examples 1-9, wherein the insulator comprises a polyether plastic.

In Example 11, the terminal connector assembly according to any one of Examples 1-10, wherein the insulator comprises Tecothane®.

In Example 12, the terminal connector assembly according to any one of Examples 1-11, wherein the D-shaped cross-section comprises a generally flat upper portion and a curved lower portion wherein a maximum depth of the D-shaped cross-section when measured between the upper flat portion and the lower curved portion is about 0.0885 inches.

In Example 13, the terminal connector assembly according to any one of Examples 1-12, wherein a maximum width of the D-shaped cross-section is equal to about 74% of an outer diameter of the terminal ring electrode.

In Example 14, the terminal connector assembly according to any one of Examples 1-13, wherein the maximum width is about 0.094 inches.

In Example 15, the terminal connector assembly according to any one of Examples 1-14, wherein a thickness of the upper portion of the terminal ring electrode is about 0.03 inches.

In Example 16, the terminal connector assembly according to any one of Examples 1-15, wherein a maximum thickness measured between an outer surface and inner surface of the first terminal ring electrode at a sidewall is about 0.01635 inches.

In Example 17, the terminal connector assembly according to any one of Examples 1-16, wherein the terminal connector assembly meets the specifications set forth in ISO/FDIS 27186 regarding IS-4 terminal connectors.

In Example 18, a medical electrical lead comprising a terminal connector assembly as recited by any one of Examples 1-17.

In Example 19, a medical electrical lead comprises a polymeric lead body including a proximal end and a distal end. At least one cable conductor extends within the lead body from the proximal end to a first electrode located on the lead body, wherein the electrode is operatively coupled to the cable conductor. A coiled conductor also extends within the lead body from the proximal end to a second electrode located on the lead body, wherein the second electrode is operatively coupled to the coiled conductor. A terminal connector assembly is coupled to the proximal end of the lead body. The terminal connector assembly comprises an inner tubular member and a terminal ring electrode disposed over the inner tubular member. The terminal ring electrode includes a first lumen having a generally D-shaped cross-section and defining a first longitudinal axis, an upper portion including a second lumen extending along a second longitudinal axis parallel the first longitudinal axis, and a blind hole having a lower surface formed in an outer surface of the upper portion such that it is disposed over the second lumen. The first terminal ring electrode also includes a lower portion including at least one aperture extending there through. The terminal connector assembly further includes an insulator and a terminal pin; wherein the cable conductor is mechanically and electrically coupled within the second lumen of the terminal ring electrode and the coiled conductor is electrically coupled to the terminal pin.

In Example 20, a method of assembling a terminal connector assembly comprises positioning a first terminal ring electrode over an inner tubular member. The first terminal ring electrode comprises a first lumen having a generally D-shaped cross-section and defining a first longitudinal axis, an upper portion including a second lumen extending along a second longitudinal axis parallel the first longitudinal axis, and a blind hole having a lower surface formed in an outer surface of the upper portion such that it is disposed over the second lumen. The first terminal ring electrode also includes a lower portion including at least one aperture extending there through. Additionally, the method comprises positioning at least a second terminal ring electrode over the tubular member such that it is radially offset from the first terminal ring electrode. The second terminal ring comprises a first lumen having a generally D-shaped cross-section and defining a first longitudinal axis, an upper portion including a second lumen extending along a second longitudinal axis parallel the first longitudinal axis, and a blind hole having a lower surface formed in an outer surface of the upper portion such that it is disposed over the second lumen. The second terminal ring electrode also includes a lower portion including at least one aperture extending there through. The method further includes the steps of molding an insulator over the inner tubular member and the first and second terminal ring electrodes, and mechanically and electrically coupling a first cable conductor to the first terminal electrode and a second cable conductor to the second terminal electrode.

In Example 21, the method according to Example 20, further comprising the step of maintaining a position of the first and second terminal ring electrodes over the inner tubular member.

In Example 22, the method according to any one of Examples 20-21, further comprising the step of inserting a core pin into the second lumens of each of the first and second terminal ring electrodes.

In Example 23, the method according to any one of Examples 20-22, wherein the step of mechanically and electrically coupling the first and second cable conductors to the first and second terminal ring electrodes, respectively, comprises applying an external, downward pressure to the lower surfaces of the blind holes provided in the outer surface of each of the inner ring electrodes.

In Example 24, the method according to any one of Examples 20-23, wherein the step of mechanically and electrically coupling the first and second cable conductors to the first and second terminal ring electrodes, respectively, comprises maintaining an outer and inner geometry of each of the first and second terminal ring electrodes.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 5A is an isometric view of a terminal ring electrode according to one embodiment of the present invention.

FIG. 5B is an end cross-sectional view taken along line 5B-5B of the terminal ring electrode shown in FIG. 5A.

FIG. 5C is a cross-sectional view taken along line 5C-5C of a portion of the terminal ring electrode shown in FIG. 5B.

Figure 1:
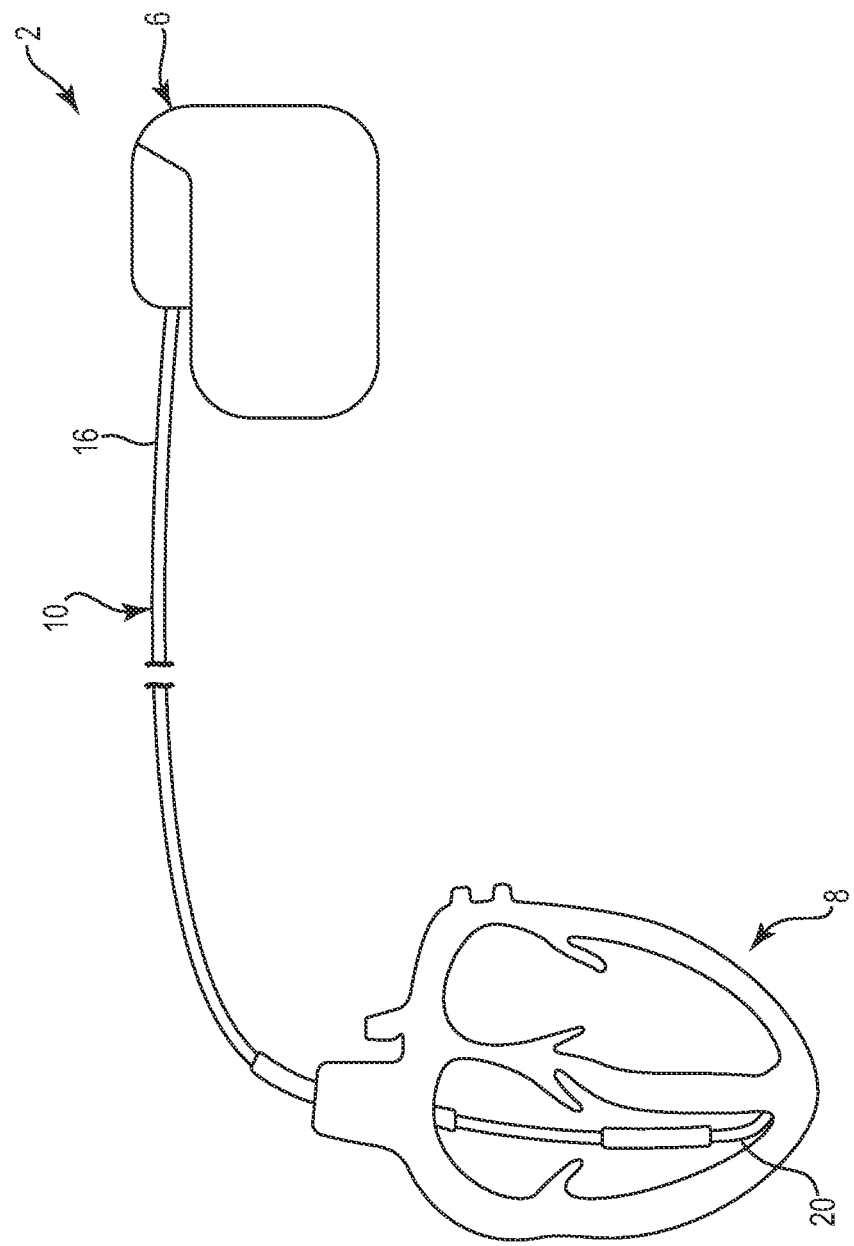
FIG. 1 is a schematic view a cardiac rhythm management system deployed at a location within a patient's heart according to an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

The leads described herein according to the various embodiments of the present invention are suitable for sensing intrinsic electrical activity and/or applying therapeutic electrical stimuli to a patient. Exemplary applications include, without limitation, cardiac rhythm management (CRM) systems and neurostimulation systems. For example, in exemplary CRM systems utilizing pacemakers, implantable cardiac defibrillators, and/or cardiac resynchronization therapy (CRT) devices, the medical electrical leads according to embodiments of the invention can be endocardial leads configured to be partially implanted within one or more chambers of the heart so as to sense electrical activity of the heart and apply a therapeutic electrical stimulus to the cardiac tissue within the heart. Additionally, the leads formed according to embodiments of the present invention may be particularly suitable for placement in a coronary vein adjacent to the left side of the heart so as to facilitate biventricular pacing in a CRT or CRT-D system. Still additionally, leads formed according to embodiments of the present invention may be configured to be secured to an exterior surface of the heart (e.g., epicardial leads).

FIG. 1 depicts a cardiac rhythm management system 2 including a pulse generator 6 coupled to a medical electrical lead 10 deployed at a location within a patient's heart 8. The pulse generator 6 is typically implanted subcutaneously within an implantation location or pocket in the patient's chest or abdomen. The pulse generator 6 may be any implantable medical device known in the art or later developed, for delivering an electrical therapeutic stimulus to the patient. In various embodiments, the pulse generator 6 is a pacemaker, a defibrillator, a cardiac resynchronization (CRT) device configured for bi-ventricular pacing, and/or includes combinations of pacing, CRT, and defibrillation capabilities.

Figure 2:
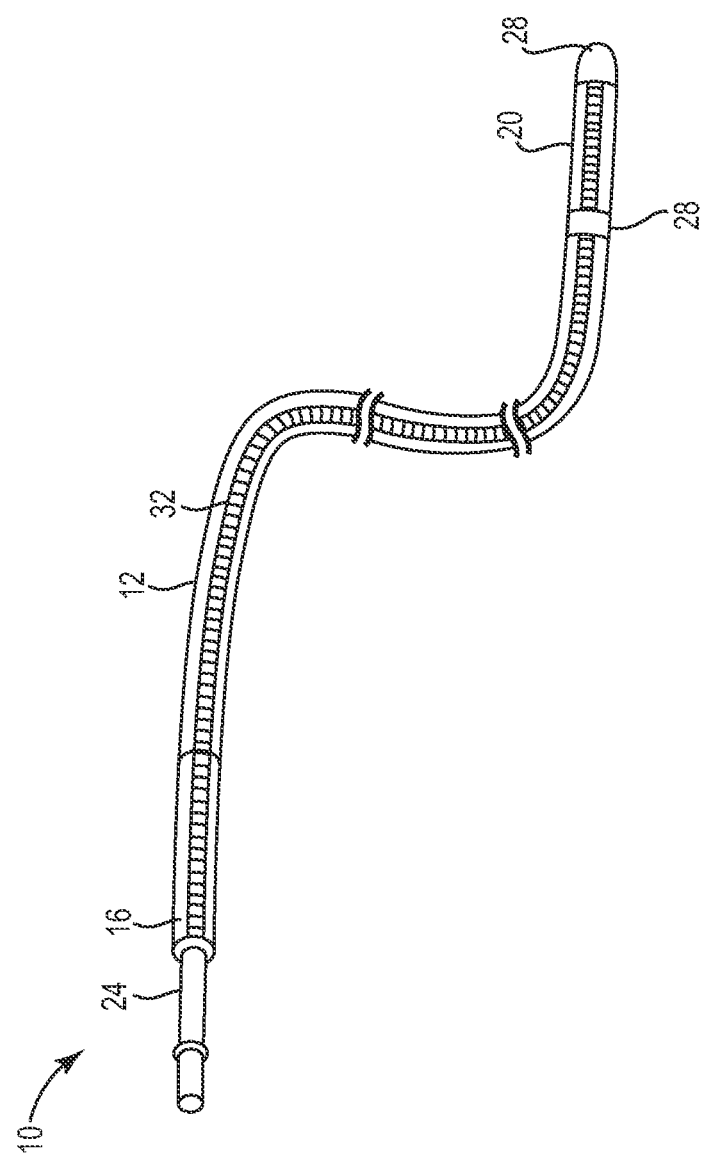
FIG. 2 is a partial cross-section view of a medical electrical lead according to an embodiment of the present invention.

FIG. 2 is a partial cross-sectional view of a medical electrical lead 10, according to various embodiments of the present invention. The medical electrical lead 10 includes an elongated lead body 12 extending from a proximal end 16 to a distal end 20. The lead body 12, according to some embodiments, is fabricated from any of a wide variety of polymeric materials including polyurethane, silicone rubber and the like. The proximal end 16 is configured to be operatively connected to a pulse generator via a connector 24. At least one conductor 32 extends from the connector 24 at the proximal end 16 of the lead 10 to one or more electrodes 28 at the distal end 20 of the lead 10. The conductor 32 can be a coiled or cable conductor. According to some embodiments where multiple conductors are employed, the lead can include a combination of coiled and cable conductors. In one embodiment, for example, the lead 10 includes a coiled conductor and three cable conductors. When a coiled conductor is employed, according to some embodiments, the conductor can have either a co-radial or a co-axial configuration.

The lead body 12 is flexible and can have a circular cross-section. Other lead body cross-sections may also be employed. According to one embodiment of the present invention, an outer diameter of the lead body 12 ranges from about 2 to about 15 French. In some embodiments, the lead body 12 may include a drug-eluting collar or plug.

The medical electrical lead 10 can be unipolar, bipolar, or multi-polar depending upon the type of therapy to be delivered. In embodiments of the present invention employing multiple electrodes 28 and multiple conductors 32, each conductor 32 is adapted to be connected to an individual electrode 28 in a one-to-one manner allowing each electrode 28 to be individually addressable. Additionally, the lead body 12 can include one or more lumens adapted to receive a guiding element such as a guidewire or a stylet for delivery of the lead 10 to a target location within a patient's heart.

The electrodes 28 can have any electrode configuration as is known in the art. According to one embodiment of the present invention, at least one electrode can be a ring or partial ring electrode. According to another embodiment, at least one electrode 28 is a shocking coil. According to yet another embodiment of the present invention, at least one electrode 28 includes an exposed electrode portion and an insulated electrode portion. In some embodiments, a combination of electrode configurations can be used. The electrodes 28 can be coated with or formed from platinum, stainless steel, MP35N, titanium, a platinum-iridium alloy, or another similar conductive material.

According to various embodiments, the lead body 12 can include one or more fixation members for securing and stabilizing the lead body 12 including the one or more electrodes 28 at a target site within a patient's body. The fixation member(s) can be active or passive. An exemplary active fixation member includes a screw-in fixation member. Examples of passive fixation members include pre-formed distal portions of the lead body 12 adapted to bear against the vessel walls and/or expandable tines provided at the distal end of the lead body 12.

Figure 3:
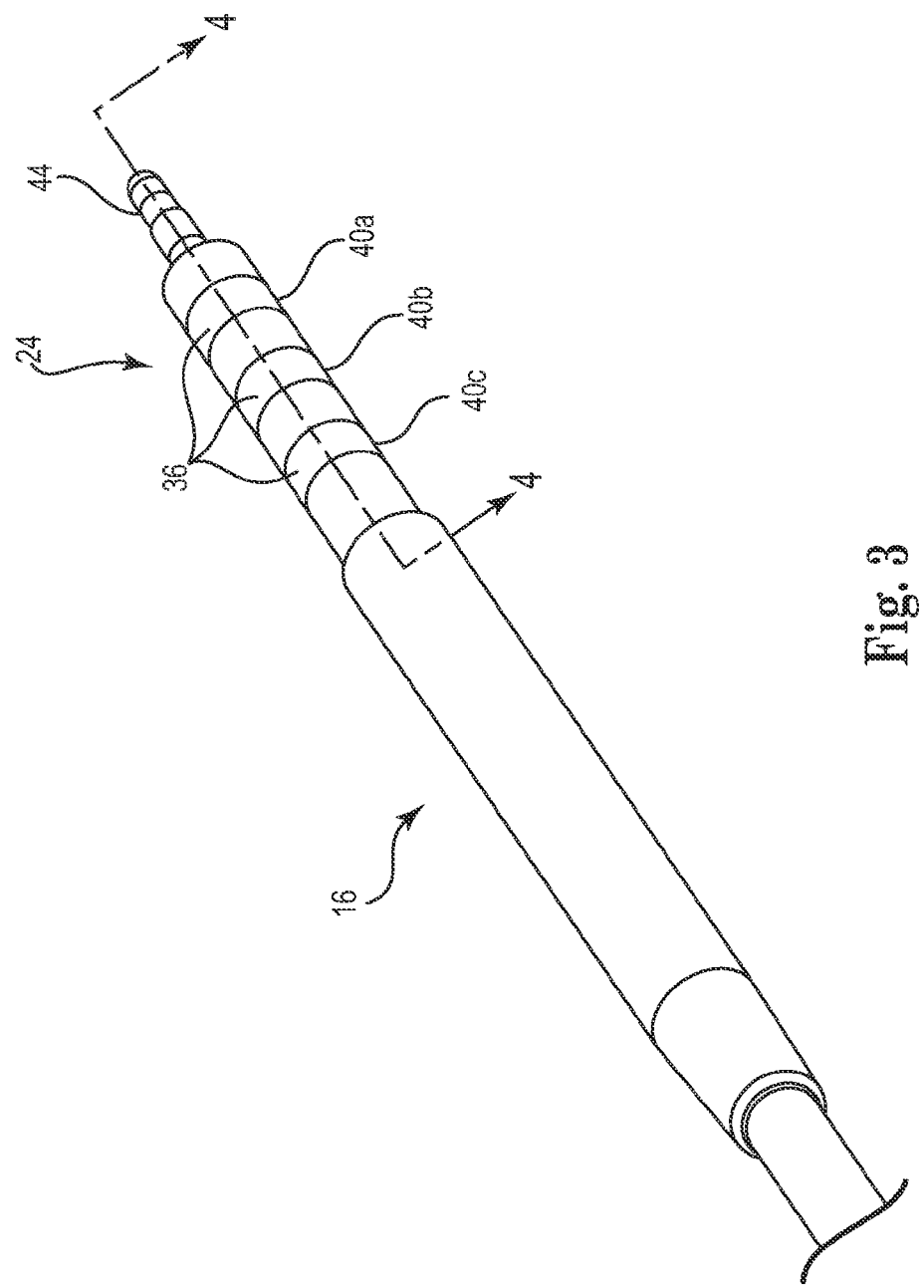
FIG. 3 is a perspective view of a portion of a medical electrical lead including a terminal connector assembly according to an embodiment of the present invention.

FIG. 3 is a schematic view of a terminal connector assembly 24. The terminal connector assembly 24, according to the various embodiments as described herein, is a quadripolar terminal connector assembly that meets the standard specifications set forth in ISO/FDIS 27186 (commonly referred to as IS-4), which is incorporated herein by reference in its entirety for all purposes. The terminal connector assembly 24 is configured to physically mate with and electrically couple to a pulse generator. In one example, the terminal connector assembly 24 includes one or more electrodes 36, such as, for example, three terminal rings 40a, 40b, and 40c. The terminal connector assembly 24 further includes a terminal pin 44. The terminal ring electrodes 40a, 40b, and 40c and the terminal pin 44 can be made from a variety of conductive materials including platinum, stainless steel, MP35N, titanium, a platinum-iridium alloy, or another similar conductive material.

According to various embodiments, each of the terminal ring electrodes 40a, 40b, and 40c are individually coupled to one of three cable conductors 52 extending within the lead body 12. The terminal ring electrodes 40a, 40b and 40c can be mechanically and electrically joined to their respective cable conductors 52 using methods such as staking, crimping, welding and the like. The terminal pin 44 is coupled to a coiled conductor 56 that extends from within the terminal connector assembly 24 through the lead body 12 from the proximal end and terminating at the most distal electrode 28 located at the distal end 20 of the lead body 12. The connection between the terminal pin 44 and the coiled conductor 56 can be achieved mechanically with methods such as welding or crimping.

Figure 4:
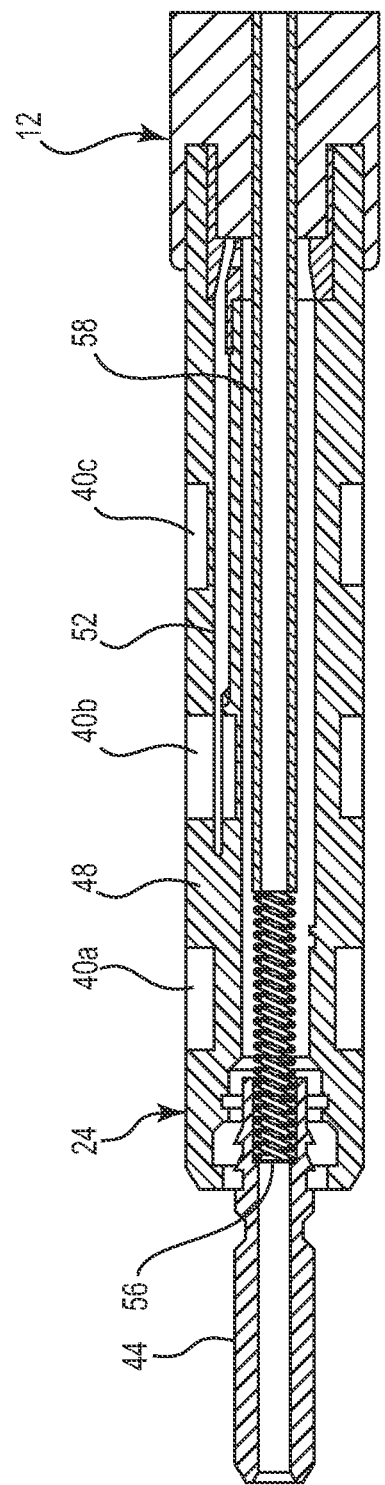
FIG. 4 is a cross-sectional view taken along line 4-4 of the terminal connector assembly shown in FIG. 3 according to an embodiment of the present invention.

FIG. 4 is a detailed, cross-sectional view of the terminal connector assembly 24 shown in FIG. 3, and depicts the middle electrode 40b electrically coupled to a cable conductor 52. As shown in FIG. 4, each of the three terminal ring electrodes, proximal 40a, middle 40b and distal 40c are disposed over an inner tubular member 58. In one embodiment, the inner tubular member 58 is a length of PEEK tubing. The terminal electrodes 40a, 40b and 40c are disposed over the inner tubular member 58 such that they are spaced apart from one another along a longitudinal axis of the terminal connector assembly 24. The distance between each of the terminal ring electrodes 40a, 40b, and 40c meets the requirements specified by the draft IS-4 standard. Additionally, the conductor 52 is spaced at a distance from the distal terminal electrode 40c such that at least one layer of the insulator 48 is disposed between the distal electrode 40c and the cable conductor 52 to prevent electrical contact between the conductor 52 and the distal electrode 40c. A polymeric material is molded around the terminal electrodes 40a, 40b and 40c, electrically isolating them from one another by one or more layers of an insulator 48. In one embodiment, the polymeric material is a polyether plastic. An exemplary polyether plastic suitable for use in the present invention is Tecothane® TT-1075D. This arrangement is repeated between each of the terminal electrodes 40a, 40b, 40c and their respective conductors 52 on the terminal connector assembly 24. Each of the terminal ring electrodes 40a, 40b and 40c have the same configuration, and are configured such that they can withstand both tensile and cyclical bending loads with minimal compromise in their outer geometry. Each of the terminal ring electrodes 40a, 40b and 40c are configured to withstand the staking load in that the cable-to-ring joint would be able to withstand tensile and cyclical bending loads encountered by the joint/assembly in implanted conditions. Additionally, each of the terminal electrodes 40a, 40b and 40c are configured such that they have both an inner and outer geometry that facilitates adequate insulation between a select terminal electrode and an adjacent conductor such as, for example, between the distal electrode 40c and cable conductor 52 shown in FIG. 4. Further, the inner geometry of each of the terminal electrodes 40a, 40b, and 40c can accommodate each of the three cable conductors 52 and the coiled conductor 56 while at the same time providing adequate insulation between each of the conductors 52 and 56 to prevent a short resulting from unwanted electrical contact between conductors.

FIGS. 5A-5C show various cross-sectional views of an exemplary terminal electrode 40a according to an embodiment of the present invention. As shown in FIGS. 5A and 5B, the terminal electrode 40a includes an outer surface 62 having a circular cross-section and an inner surface 66 defining a first major lumen 70 having a central longitudinal axis 74. Additionally, the terminal electrode 40a includes a second lumen 78 formed in an upper portion 82 of the terminal electrode 40a such that it extends along a longitudinal axis 88 parallel to the central longitudinal axis 74 defined by the first major lumen 70. According to various embodiments, the terminal electrode also includes a blind hole 86 formed in the outer surface 62 of the upper portion 82 of the terminal electrode 40a such that it is disposed over the second lumen 78. In one embodiment, a thickness l1 of the upper portion 82 is approximately 0.03 inches. In some embodiments, the terminal electrode 40a further includes one or more apertures 92 formed in a lower portion 96 of the terminal electrode such that the apertures 92 extend through the terminal electrode 40a from the outer surface 62 to the inner surface 66.

In various embodiments of the present invention, the terminal electrode 40a is configured such that the outer diameter of the terminal electrode 40a does not substantially change when the cable conductor is electrically and mechanically coupled to the terminal electrode 40a. In one embodiment an outer diameter of the terminal electrode 40a ranges from about 0.1263 inches to about 0.1271 inches.

According to one exemplary embodiment of the present invention, as shown in FIGS. 5A and 5B, the first major lumen 70 has a generally D-shaped cross-section. The inner surface 66 of the terminal electrode 40c defining the D-shaped cross-section includes an upper, generally flat portion 104 and a lower, generally curved portion 108. In one embodiment, the depth of the D-shaped cross-sectional profile l2 is approximately 0.08885 inches. Additionally, the inner surface 66 defines first and second sidewalls 112, 114 connecting the upper, generally flat portion 104 to the lower generally curved portion 108. In one embodiment, a maximum width, w1, measured between the first and second side walls 112, 114 is equal to about 74% of the outer diameter of the terminal electrode 40a. In another embodiment, a maximum width w1 is about 0.094 inches. In another embodiment, a maximum width w2 of each of the sidewalls 112, 114 is 0.01635 inches. As shown in FIG. 5B, the inner surface 66 also defines a curved transition 116, 118 from the first and second side walls 112, 114, respectively, to the upper generally, flat portion 104. In one embodiment the radius of curvature of the curved transition is approximately 0.011 inches.

As shown in FIGS. 5A-5C, the second lumen 78 extends through the upper portion 82 of the terminal electrode 40c along a central axis parallel to the central longitudinal axis 74 extending within the first lumen 70. According to various embodiments, the second lumen 78 has a substantially circular cross-section and is adapted to receive at least a non-insulated portion of a cable conductor therein. In one embodiment an inner diameter of the second lumen ranges from about 0.0060 to about 0.0070 inches. In some embodiments, the second lumen 78 is closer in proximity to the inner surface 66 of the terminal electrode 40a than the outer surface 62. That is, the distance between the inner surface 66 and central axis of the second lumen 78 is less than the distance between the outer surface 62 and the central axis of the second lumen 78.

According to various embodiments, the terminal electrode 40a also includes a blind hole 86 formed in the outer surface 62 of the upper portion 82 of the terminal electrode 40a. As best shown in FIGS. 5B and 5C, the blind hole 86 is formed in the upper portion 82 of the terminal electrode such that it is disposed over the second lumen 78. More particularly, the blind hole 86 is disposed over the second lumen 78 such that a central axis 122 of the blind hole 86 is perpendicular to the central axis 88 of the conductor lumen 78. The depth of the blind hole 86 is defined such that the material thickness between a lower surface 126 of the blind hole 86 and the second lumen 78 can be deformed to retain the cable conductor therein for optimal joint strength without significantly compromising the outer and inner geometries of the terminal connector 40a, described above. Additionally, the blind hole 86 facilitates external staking of the cable conductor in the second lumen 78.

Additionally, in some embodiments, the terminal electrode 40a includes one or more apertures 92 formed in the outer surface 62 of a lower portion 96 of the terminal electrode 40a. The apertures 92 extend through the electrode 40a from the outer surface 62 to the inner surface 66. In one embodiment, as shown in FIG. 5B, a first aperture 92 is located on the lower portion 96 of the terminal electrode 40a in axial alignment with the second conductor lumen and the blind hole 86. The second and third apertures 92 are spaced at an equal distance from the first aperture 92. In one embodiment, the second and third apertures 92 are spaced from the first aperture 92 at an angle α measured through the central axis 74 of greater than about 90°. In one embodiment, the second and third apertures 92 are spaced from the first aperture 92 at an angle α measured through the central axis 74 of less than about 90°. In another embodiment, the second and third apertures 92 are space from the first aperture 92 at an angle α of about 64°. During the assembly process, which will be described in greater detail below, a pin can be inserted through a selected aperture 92 to hold the terminal ring electrode 40a in a desired position relative to the other terminal ring electrodes 40b and 40c.

Figure 6A:
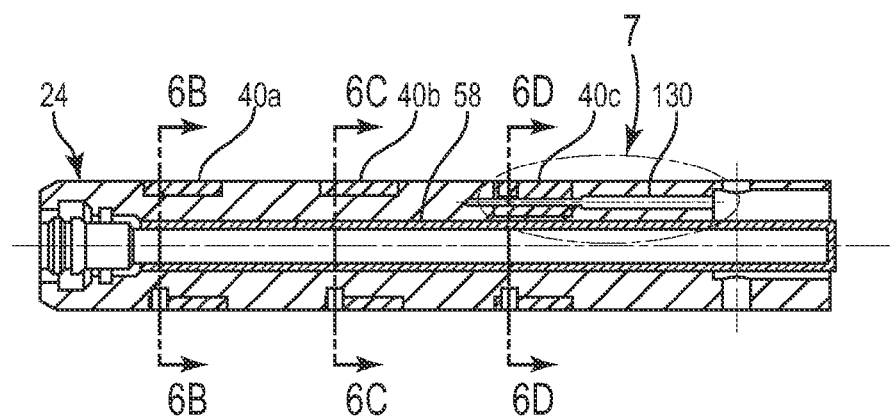
FIG. 6A is a longitudinal cross-sectional view of a terminal connector assembly excluding the conductors according to one embodiment of the present invention.
Figure 6B:
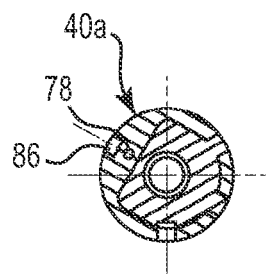
FIGS. 6B-6D are cross-section views taken along lines 6B-6B, 6C-6C and 6D-6D, respectively, of the terminal connector assembly including the terminal ring electrodes shown in FIG. 6A.
Figure 6C:
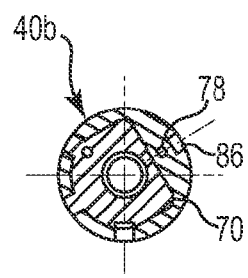
Figure 6D:
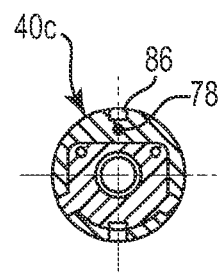

FIG. 6A is a cross-sectional view of the terminal connector assembly 24 excluding the terminal pin 44 and conductors 52 and 56. FIGS. 6B-6D are cross-sectional views of each of the terminal ring electrodes 40a, 40b and 40c located on the terminal connector assembly 24. FIGS. 6B-6D show the position of each of the conductor lumens 78 of the different electrodes 40a, 40b and 40c relative to one another. According to various embodiments of the invention, each of the terminal ring electrodes 40a, 40b and 40c are positioned on the terminal connector assembly 24 such that their conductor lumens 78 are radially offset from one another. More specifically, the terminal electrodes 40a, 40b and 40c are positioned on the terminal electrode assembly 24 such that their conductor lumens 78 are radially offset from one another by less than about 90°. In a further embodiment, the electrodes 40a, 40b and 40c are positioned on the terminal electrode assembly 24 such that their conductor lumens 78 are radially offset from one another by between about 50° and about 70° (e.g., about 64°). By positioning the terminal electrodes 40a, 40b and 40c on the terminal connector assembly 24 such that their conductor lumens 78 are offset from one another, the arrangement of the electrodes 40a, 40b and 40c together with the D-shaped cross-sectional profile of the first lumen 70 can accommodate multiple cable conductors and provide adequate space for insulation between each of the multiple cable conductors which can prevent an electrical short. Additionally, according to various embodiments of the present invention, the terminal connector assembly 24 includes one or more conductor lumens 130. In one embodiment, the terminal connector assembly 24 includes three conductor lumens 130, one lumen for each of the three cable conductors 52 extending within the terminal connector assembly 24. An exemplary conductor lumen 130 is shown in FIG. 6A, and in greater detail in FIG. 7. As shown in FIG. 6A, the conductor lumen 130 extends parallel to the central axis 74. In another embodiment, the distal portion of the conductor lumen 138 is offset axially from axes of lumens 134 and 78.

Figure 7:
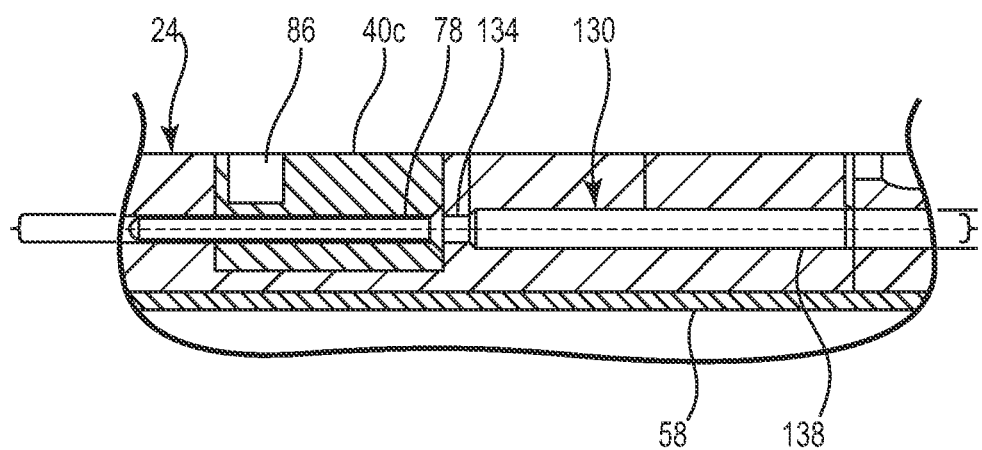
FIG. 7 is a detailed, cross-sectional view of a portion of the terminal connector assembly shown in FIG. 6A.

As shown in FIG. 7, each conductor lumen 130 includes a first portion 134 and a second portion 138. In one embodiment, the first portion 134 is smaller in diameter than the second portion 138, and is adapted to receive a non-insulated portion of the cable conductor 52. In one embodiment, the diameter of the first portion 134 of the conductor lumen 130 ranges from about 0.0060 inches to about 0.0070 inches, and the diameter of the second portion 138 ranges from about 0.0103 inches to about 0.0107 inches. In some embodiments, the conductor lumen 130 can include a neck-down or tapered region as the conductor lumen 130 transitions in diameter from the larger diameter second portion 138 to the smaller diameter first portion 134. This configuration aids in the overall assembly of the terminal connector assembly 24, and facilitates stringing of the cable conductors 52 through the lumens 130.

When inserted into the terminal connector assembly 24, the non-insulated portion of the conductor 52 (not shown) extends from the first portion 134 of the lumen and through the second lumen 78 provided in the terminal ring electrode 40c. The second portion 138 of the lumen 130 is large enough to accommodate the insulated portion of the conductor 52. Electrical and mechanical contact between the terminal ring electrode 40c is made by externally staking the cable conductor 52 by deforming the material between the blind hole 86 and the second lumen 78.

Figure 8:
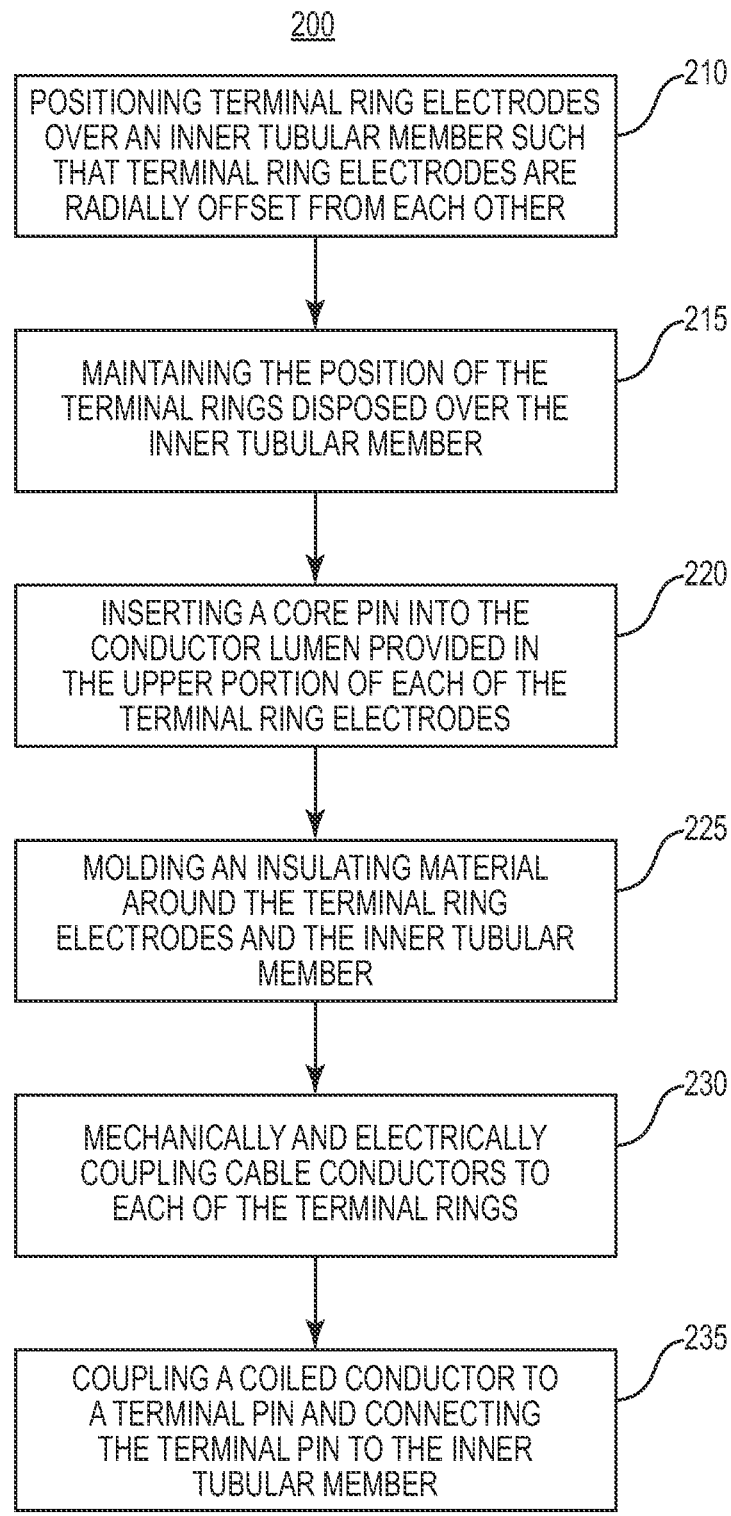
FIG. 8 is a flow chart of a method of assembling a terminal connector assembly according to one embodiment of the present invention.

FIG. 8 is a flow chart of a method 200 of assembly of a terminal connector assembly according to the various embodiments of the present invention. The three terminal rings electrodes are positioned over an inner tubular member (Block 210). In one embodiment, the inner tubular member is a length of PEEK tubing. In one embodiment, the terminal ring electrodes are positioned over the inner tubular member such that each are spaced about 0.100 inches in the longitudinal direction. Additionally, the terminal ring electrodes are positioned over the inner tubular member such that they are radially offset from one another (Block 210). In one embodiment, each of the terminal electrodes are radially offset by about 64° in the radial direction from each other. In some embodiments, pins may be inserted through one of the apertures provided in the terminal ring electrode to maintain the position of each terminal ring electrode relative to one another (Block 215).

Prior to molding an insulating material around the terminal conductor rings and inner tubular member, core pins are inserted in to each of the conductor lumens provided in the upper portion of the terminal electrodes (Block 220). The core pins aid in the formation of each of the conductor lumens needed for stringing the cable conductors. According to various embodiments, the core pins have a diameter greater than a diameter of an insulated portion of a cable conductor to ensure the stringability of the cable conductors. In one embodiment, the core pins are approximately 0.0105 inches in diameter. Due to the small size of these core pins, removal of the pins after the molding step may be difficult. Furthermore, the durability and longevity of these small core pins may be low. To mitigate this issue, the core pins can include a draft or tapered region, wherein a diameter of a distal pin portion is greater than a diameter of a proximal pin portion. This aids with removal of the core pins. In a further embodiment, the draft or tapered core pins are inserted into the conductor lumens of the proximal and middle terminal ring electrodes to form a tapered or eccentric conductor lumen. To maintain adequate clearance between the core pins and terminal ring electrodes during the molding step, the drafted or tapered core pins are skewed towards the central axis of the terminal connector assembly.

The terminal connector body is formed by injecting an insulating material to fill the space between the inner tubular member and the terminal ring electrodes (Block 225). The cured and annealed insulating material also provides insulation between each of the cable conductors extending within the terminal connector body. In one embodiment, a polyether plastic such as, for example Tecothane® TT-1075D-M, is injected at high temperature and pressure to fill the space between the inner tubular member and the terminal ring electrodes. Molding the terminal connector body provides the flexibility in lead assembly sequence. For example, the lead can be assembled from the distal end towards the proximal end and vice versa. Additionally, assembling the terminal connector body without the cable conductors facilitates a potential cost-savings if nonconforming parts should occur and the terminal connector body needs to be discarded.

After the insulating material has been annealed and cured to form the terminal connector assembly body, the core pins are removed leaving behind conductor lumens for each of the cable conductors. The cable conductors are then inserted into each of the conductor lumens. In one embodiment, the conductor lumens can be backfilled with a medical adhesive to further electrically isolate each of the cable conductors.

Next, the cable conductors are mechanically and electrically coupled to each of the terminal ring electrodes on the terminal connector assembly (Block 230). In one embodiment, the mechanical and electrical joint between the cable conductors and each of the terminal ring electrodes and rings is achieved by staking a non-insulated portion of the cable conductor hole within the conductor lumen provided in the upper portion of the terminal ring electrode. The cable conductor is staked by deforming a portion of the terminal ring electrode material to contact and secure the non-insulated portion of the cable conductor located within (Block 230). In one embodiment, the cable conductor is staked externally by applying a downward pressure to the blind hole formed in the outer surface of the terminal ring electrode and deforming the material between the blind hole and the conductor lumen provided in the terminal ring electrode until the conductor lumen contacts the non-insulated portion of the cable conductor inserted therein. In one embodiment, the depth of the blind hole is defined such that the material thickness between the blind hole and conductor lumen provided in the terminal ring electrode can be deformed to retain the cable conductor therein without significantly compromising the other features or geometries on the terminal ring electrode.

After the three cable conductors are electrically coupled to their respective terminal ring electrodes, the terminal pin is coupled to the coiled conductor inserted within the lumen of the inner tubular member (Block 235). In one embodiment, the terminal pin can be welded to the coiled conductor. The terminal pin is then snap-fit to the inner tubular member (Block 235). Finally, the terminal connector assembly can be coupled to the lead body to form the medical electrical lead.

A lead including the terminal connector assembly described above according to the various embodiments is introduced within the vasculature of a patient and delivered to a target location within a patient's heart. An energy source such as, for example, a pulse generator, is implanted subcutaneously within the patient. The terminal connector assembly is inserted into a socket provided in the pulse generator to electrically couple the terminal connector assembly to the pulse generator.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A terminal connector assembly for a medical electrical lead comprising:
   an inner tubular member;
   a first terminal ring electrode disposed over the inner tubular member, the terminal ring electrode comprising: a first lumen having a generally D-shaped cross-section and defining a first longitudinal axis; an upper portion of the first terminal ring electrode including a second lumen extending along a second longitudinal axis parallel the first longitudinal axis and a blind hole having a lower surface formed in an outer surface of the upper portion such that the blind hole is disposed over the second lumen; and a lower portion of the first terminal ring electrode including at least one aperture extending there through;
   a first cable conductor mechanically and electrically coupled within the second lumen of the first terminal ring electrode;
   a second terminal ring electrode disposed over the inner tubular member such that the second terminal ring electrode is radially offset from the first terminal ring electrode;
   an insulator disposed over the inner tubular member and between the first and second terminal ring electrodes such that the first and second terminal ring electrodes are electrically isolated from one another; and
   wherein the D-shaped cross-section comprises a flat upper portion and a curved lower portion having a maximum depth of the D-shaped cross-section between the upper flat portion and the lower curved portion.

2. The terminal connector assembly according to claim 1, wherein the second terminal ring electrode comprises a first lumen having a generally D-shaped cross-section and defining a first longitudinal axis, an upper portion including a second lumen extending along a second longitudinal axis parallel the first longitudinal axis and a blind hole formed in an outer surface of the upper portion such that it is disposed over the second lumen, and a lower portion including at least one aperture extending there through.

3. The terminal connector assembly according to claim 1, wherein the second terminal ring electrode is radially offset from the first terminal ring electrode by about 64°.

4. The terminal connector assembly according to claim 1, further comprising a second cable conductor mechanically and electrically coupled to the second terminal ring electrode.

5. The terminal connector assembly according to claim 1, further comprising a third terminal ring electrode disposed over the inner tubular member such that the third terminal ring electrode is radially offset from the second terminal ring electrode and wherein the third terminal ring electrode is electrically isolated by the insulator from the first and second terminal ring electrodes.

6. The terminal connector assembly according to claim 1 further comprising a terminal pin coupled to a coiled conductor extending within the inner tubular member.

7. The terminal connector assembly according to claim 1, wherein the insulator comprises a polyether plastic.

8. The terminal connector assembly according to claim 1, wherein the maximum depth of the D-shaped cross-section when measured between the upper flat portion and the lower curved portion is about 0.0885 inches.

9. The terminal connector assembly according to claim 1, wherein a maximum width of the D-shaped cross-section is equal to about 74% of an outer diameter of the terminal ring electrode.

10. The terminal connector assembly according to claim 1, wherein the maximum width is about 0.094 inches.

11. The terminal connector assembly according to claim 1, wherein a thickness of the upper portion of the terminal ring electrode is about 0.03 inches.

12. The terminal connector assembly according to claim 1, wherein a maximum thickness measured between an outer surface and inner surface of the first terminal ring electrode at a sidewall is about 0.01635 inches.

13. The terminal connector assembly according to claim 1, wherein the terminal connector assembly meets the specifications set forth in ISO/FDIS 27186 regarding IS-4 terminal connectors.

14. A medical electrical lead comprising a terminal connector assembly as recited by claim 1.

* * * * *